(12) United States Patent
Buckland et al.

(10) Patent No.: US 7,847,951 B2
(45) Date of Patent: Dec. 7, 2010

(54) SPECTRAL DOMAIN PHASE MICROSCOPY (SDPM) DUAL MODE IMAGING SYSTEMS AND RELATED METHODS AND COMPUTER PROGRAM PRODUCTS

(75) Inventors: Eric L. Buckland, Hickory, NC (US); Seungbum Woo, Durham, NC (US); Joseph A. Izatt, Raleigh, NC (US); William J. Brown, Durham, NC (US)

(73) Assignee: Bioptigen, Inc., Durham, NC (US)

( * ) Notice: Subject to any disclaimer, the term of this patent is extended or adjusted under 35 U.S.C. 154(b) by 0 days.

(21) Appl. No.: 12/477,949

(22) Filed: Jun. 4, 2009

(65) Prior Publication Data

US 2009/0237673 A1    Sep. 24, 2009

Related U.S. Application Data

(62) Division of application No. 11/560,175, filed on Nov. 15, 2006, now Pat. No. 7,554,669.

(60) Provisional application No. 60/736,945, filed on Nov. 15, 2005.

(51) Int. Cl.
*G01B 9/02* (2006.01)
*G01B 11/02* (2006.01)

(52) U.S. Cl. .................................. 356/479; 356/497

(58) Field of Classification Search ............ 356/479, 356/497
See application file for complete search history.

(56) References Cited

U.S. PATENT DOCUMENTS

| 7,301,644 | B2 | 11/2007 | Knighton et al. |
| 2005/0018201 | A1 | 1/2005 | de Boer et al. |
| 2006/0256343 | A1* | 11/2006 | Choma et al. ............... 356/450 |
| 2007/0002327 | A1 | 1/2007 | Zhou et al. |
| 2007/0291277 | A1 | 12/2007 | Everett et al. |

FOREIGN PATENT DOCUMENTS

WO    WO 2006/078839 A2    7/2006

OTHER PUBLICATIONS

Choma et al., "Spectral-domain phase microscopy," Optics Letters, vol. 30, No. 10, May 15, 2005, 1162-1164.
Danielson et al., "Guided-wave reflectometry with micrometer resolution," Applied Optics, vol. 26, No. 14, Jul. 15, 1987, 2836-2842.
Joo, Chulmin, "Spectral-domain optical coherence phase microscopy for quantitative phase-contrast imaging," Optics Letters, vol. 30, No. 16, Aug. 15, 2005, 2131-2133.

(Continued)

*Primary Examiner*—Michael A Lyons
(74) *Attorney, Agent, or Firm*—Myers Bigel Sibley & Sajovec (57) ABSTRACT

Some embodiments of the present invention provide optical coherence tomography systems including an OCT engine and a processor. The OCT engine is configured to provide both standard OCT imaging and spectral domain phase microscopy (SDPM) imaging. The processor is coupled to the OCT engine and is configured to use a first signal processing method when the OCT engine is configured to provide standard OCT imaging and a second signal processing method when the OCT engine is configured to provide SDPM imaging. Related methods and computer program products are also provided.

4 Claims, 12 Drawing Sheets

OTHER PUBLICATIONS

Takada et al., "New measurement system for fault location in optical waveguide devices based on an interferometric technique," Applied Optics, Vo. 26, No. 9, May 1, 1987, 1603-1606.

Youngquist et al., "Optical coherence-domain reflectometry: a new optical evaluation technique," Optics Letters, vol. 12, No. 3, Mar. 1987, 158-160.

Invitation to Pay Additional Fees—Communication Relating to the Results of the Partial International Search, corresponding to International Application No. PCT/US2006/044332, mailed Apr. 11, 2007.

Notification of Transmittal of the International Search Report and the Written Opinion of the International Searching Authority, or the Declaration, International Application No. PCT/US2006/044332; Jun. 28, 2007.

Ellerbee et al., "Characterizing cellular contractility and cytoplasmic flow using spectral domain phase microscopy," Proceedings of SPIE, vol. 5690, Apr. 2005, 403-407.

Hitzenberger et al., "Imaging of cell layers by differential phase contrast optical coherence microscopy," Proceedings of SPIE, vol. 4956, Jul. 2003, 22-24.

Invitation to Pay Additional Fees - Communication Relating to the Results of the Partial International Search, corresponding to International Application No. PCT/US2006/044332, mailed Apr. 11, 2007.

* cited by examiner

SPECTRAL DOMAIN PHASE MICROSCOPY (SDPM) DUAL MODE IMAGING SYSTEMS AND RELATED METHODS AND COMPUTER PROGRAM PRODUCTS

CLAIM OF PRIORITY

The present application is a divisional of U.S. patent application Ser. No. 11/560,175, filed Nov. 15, 2006 now U.S. Pat. No. 7,554,669, which claims priority from U.S. Provisional Application No. 60/736,945, filed Nov. 15, 2005, the disclosures of which are hereby incorporated herein by reference as if set forth in their entirety.

FIELD OF THE INVENTION

The present invention relates to imaging and, more particularly, to optical coherence imaging devices, methods and systems.

BACKGROUND OF THE INVENTION

Since its introduction in the early 1990's, optical coherence tomography (OCT) has emerged as a promising imaging modality for micrometer-scale noninvasive imaging in biological and biomedical applications. Its relatively low cost and real-time, in vivo capabilities have fueled the investigation of this technique for applications in retinal and anterior segment imaging in ophthalmology (e.g., to detect retinal pathologies), early cancer detection and staging in the skin, gastrointestinal, and genitourinary tracts, as well as for ultrahigh resolution imaging of entire animals in embryology and developmental biology.

Conventional OCT systems are essentially range-gated low-coherence interferometers that have been configured for characterization of the scattering properties of biological and other samples. By measuring singly backscattered light as a function of depth, OCT fills a valuable niche in imaging of tissue ultrastructure, and provides subsurface imaging with high spatial resolution (~1-10 µm) in three dimensions and high sensitivity (>110 dB) in vivo with no contact needed between the probe and the tissue. OCT is based on the one-dimensional technique of optical coherence domain reflectometry (OCDR), also called optical low-coherence reflectometry (OLCR). See Youngquist, R. C., S. Carr, and D. E. N. Davies, *Optical Coherence Domain Reflectometry: A New Optical Evaluation Technique*. Opt. Lett., 1987. 12: p. 158; Takada, K., et al., *New measurement system for fault location in optical waveguide devices based on an interferometric technique*. Applied Optics, 1987. 26(9): p. 1603-1606; and Danielson, B. L. and C. D. Whittenberg, *Guided-wave Reflectometry with Micrometer Resolution*. Applied Optics, 1987. 26(14): p. 2836-2842. In some instances of time-domain OCT, depth in the sample is gated by low coherence interferometry. The sample is placed in the sample arm of a Michelson interferometer, and a scanning optical delay line is located in the reference arm.

The time-domain approach used in conventional OCT has been used in supporting biological and medical applications. An alternate approach involves acquiring as a function of optical wavenumber the interferometric signal generated by mixing sample light with reference light at a fixed group delay. Two methods have been developed which employ this Fourier domain (FD) approach. The first is generally referred to as Spectral-domain OCT (SD-OCT). SD-OCT uses a broadband light source and achieves spectral discrimination with a dispersive spectrometer in the detector arm. The second is generally referred to as swept-source OCT (SS-OCT). SS-OCT time-encodes wavenumber by rapidly tuning a narrowband source through a broad optical bandwidth. Both of these techniques can provide improvements in SNR of up to 15-20 dB when compared to time-domain OCT, because SD-OCT and SS-OCT capture the complex reflectivity profile (the magnitude of which is generally referred to as the "A-scan" data or depth-resolved sample reflectivity profile) in parallel. This is in contrast to time-domain OCT, where destructive interference is employed to isolate the interferometric signal from only one depth at a time as the reference delay is scanned.

However, the resolution of current OCT techniques is generally limited by the coherence length of the illumination source. Therefore, current OCT techniques may not be able to resolve structures of less than ~1-10 µm. For example, the characteristics and dynamics of the cellular surface may be of interest in many areas of quantitative biology. However, there are few scientific tools which are capable of noninvasively acquiring quantitative information about cell surface profiles, displacements, and motions on the nanometer scale.

Recent advances have increased the imaging speed, which may allow relatively large image sets (such as 3-D volumes) to be quickly generated. Since OCT is high-speed, non-contact and non-destructive, it is well suited for imaging dynamics over short time scales, for example, well below 1 second (the beating of a heart tube in a fruit fly) all the way Up to changes over a long time scales, for example, days or even longer (tissue growing).

Spectral domain phase microscopy (SDPM) is an extension of SD-OCT (38-40) which may allow for the measurement of nanometer-scale displacements and motions within each pixel of an SD-OCT image. The major modifications in SDPM as compared to SD-OCT are the substitution of a common path interferometer for the Michelson interferometer in SD-OCT, and enhanced signal processing based on the measured phase of the SD-OCT signal in each image pixel to extract nanometer-scale displacement and motion of reflectors and scatterers located within that pixel. SDPM has been discussed in, for example, "Spectral-domain phase microscopy" by M. A. Choma, A. K. Ellerbee, C. Yang, T. L. Creazzo, and J. A. Izatt, Opt. Lett. 30(10), 1162 (2005) and "Spectral-domain optical coherence phase microscopy for quantitative phase-contrast imaging" by C. Joo, T. Akllin, B. Cense, B. H. Park, and J. F. DeBoer, Opt. Lett. 30(16), 2131 (2005).

SUMMARY OF THE INVENTION

Some embodiments of the present invention provide optical coherence tomography systems including an OCT engine and a processor. The OCT engine is configured to provide both standard OCT imaging and spectral domain phase microscopy (SDPM) imaging. The processor is coupled to the OCT engine and is configured to use a first signal processing method when the OCT engine is configured to provide standard OCT imaging and a second signal processing method when the OCT engine is configured to provide SDPM imaging.

In further embodiments of the present invention, a scanning sample probe may be coupled to the OCT engine and may be configured to provide lateral scanning of a sample and provide image information associated with the sample. In certain embodiments of the present invention, the scanning sample probe may include single mirrors, galvo mirror pairs and/or microelectromechanical mirrors.

In still further embodiments of the present invention, the image information associated with the sample may include features in the sample larger than a resolution of from about 3.0 to about 10.0 µm.

Some embodiments of the present invention provide spectral domain phase microscopy (SDPM) systems including a transparent member and a scanning sample probe. The transparent member is positioned on a sample. A sample probe and a sample stage are configured to provide image information through the transparent member of the sample such that image information associated with a first surface of the sample can be distinguished from image information associated with a second surface of the sample.

In further embodiments of the present invention, the sample probe may be configured to provide lateral scanning of the sample.

In still further embodiments of the present invention, the sample stage may include a moveable sample stage. The sample may be positioned on the movable stage such that the moveable sample stage provides lateral scanning with respect to the sample probe.

In some embodiments of the present invention, one or more spacers may be positioned between the transparent member and the scanning sample. A distance provided by the one or more spacers between the sample and the transparent member may be used to distinguish between the image information associated with a first surface of the sample and the image information associated with a second surface of the sample. The distance between the sample and the transparent member may be adjustable. In certain embodiments of the present invention, the distance between the sample and the transparent member may be less than a thickness of the sample.

In further embodiments of the present invention, the distance between the sample and the transparent member may be greater than a resolution of the OCT-configured imaging system.

In still further embodiments of the present invention, the transparent member may be a glass slide or a glass slide having an antireflective coating on at least one surface of the glass slide. The glass slide may be optically flat to within a fraction of a wavelength of the imaging system. The uncoated glass slide may have a thickness of about 4.0 mm, about a depth window of the OCT imaging system or about at least thicker than the sample.

In some embodiments of the present invention, the transparent member may be an integral component of a sample structure. The transparent member may be delineated from a remainder of the sample structure by a regular boundary observable with the OCT imaging system.

In further embodiments of the present invention, the system may further include an OCT engine and a processor. The OCT engine may be coupled to the scanning sample probe and may be configured to provide both standard OCT imaging and SDPM imaging. The processor may be coupled to the OCT engine and configured to use a first signal processing method when the OCT engine is configured to provide standard OCT imaging and a second signal processing method when the OCT engine is configured to provide SDPM imaging.

Still further embodiments of the present invention provide OCT systems including an OCT engine, a processor, a scanning sample probe, a sample stage and a transparent member. The OCT engine is configured to provide both standard OCT imaging and spectral domain phase microscopy (SDPM) imaging. The processor is coupled to the OCT engine and configured to use a first signal processing method when the OCT engine is configured to provide standard OCT imaging and a second signal processing method when the OCT engine is configured to provide SDPM imaging. The scanning sample probe and the scanning sample stage are coupled to the OCT engine. The transparent member is positioned on a sample. The scanning sample probe and the scanning sample stage are configured to provide lateral scanning of the sample through the transparent member and provide image information associated with the sample such that image information associated with a first surface of the sample can be distinguished from image information associated with a second surface of the sample.

Some embodiments of the present invention provide OCT systems including an OCT engine and a processor. The OCT engine is configured to provide both standard OCT imaging and spectral domain phase microscopy (SDPM) imaging, obtain image data associated with a first pass through a sample and obtain image data associated with a second pass through the sample. The processor is coupled to the OCT engine and configured to process the image data associated with the first and second passes through the sample to determine a path length variation and provide an image having a resolution based on the determined path length variation.

Further embodiments of the present invention provide methods of processing OCT data. Both standard OCT imaging and spectral domain phase microscopy (SDPM) imaging are provided using a single OCT engine using a first signal processing method when the OCT engine is configured to provide standard OCT imaging and a second signal processing method when the OCT engine is configured to provide SDPM imaging.

In still further embodiments of the present invention, raw data associated with a sample from the OCT engine may be received at a processor. The DC background data may be subtracted from the raw data. Data remaining after the DC subtraction may be resampled to convert from sampling in wavelength space to sampling in wavenumber space. The resampled data may be Fourier transformed to transform wavenumber space to amplitude data and/or phase data. The second processing method may include selecting phase data from a particular depth in the sample. Phase change and unwrapping operations may be performed with respect to the selected phase data. The phase changed and unwrapped data may be scaled to provide an SDPM image.

In some embodiments of the present invention, the first processing method may include resealing the amplitude data to generate a standard OCT image.

Further embodiments of the present invention provide methods for imaging a sample and a transparent member positioned on a sample using SDPM. Image information is obtained from the sample when the sample is in a first position and one or more surfaces of the transparent member provides one or more first interfaces for SDPM measurements of the sample in the first position and depths in the sample provide one or more second interfaces for the SDPM measurements of the sample in the second position. Image information is obtained from the sample when the sample is in a second position. One or more surfaces of the transparent member provides at one or more first interfaces for SDPM measurements of the sample in the second position and depths in the sample provide one or more second interfaces for the SDPM measurements of the sample in the second position. The first position of the sample and the second position of the sample are distinguished based on the image information obtained from the sample in the first and second positions.

In still further embodiments of the present invention, image information may be obtained from the sample in the first position by obtaining an image depicting spacing between the transparent member and the sample in the first position, obtaining an image depicting a thickness of the sample in the first position and obtaining an image depicting a sum of the spacing between the transparent member and the sample in the first position and the thickness of the sample in the first position.

In some embodiments of the present invention, image information from the sample in the second position may be obtained by obtaining an image depicting spacing between the transparent member and the sample in the second position, obtaining an image depicting a thickness of the sample in the second position, and obtaining an image depicting a sum of the spacing between the transparent member and the sample in the second position and the thickness of the sample in the second position.

In further embodiments of the present invention, the obtained images from the sample in the first and second positions may be processed to provide distinguishable images of the first and the second surfaces of sample.

Still further embodiments of the present invention provide methods for acquiring high resolution SDPM by obtaining image data associated with a first pass through a sample and obtaining image data associated with a second pass through the sample. The image data associated with the first and second passes through the sample are processed to determine a path length variation. An image having a resolution based on the determined path length variation is provided.

In some embodiments of the present invention, path length may be directly proportional to the resolution of the image.

Although embodiments of the present invention are primarily discussed above with respect to systems and methods, related computer program products are also provided herein.

DETAILED DESCRIPTION OF THE INVENTION

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Some embodiments of the present invention will now be discussed with respect to FIGS. 1 through 12. As illustrated therein, some embodiments of the present invention consist of novel system designs for Spectral Domain Phase Microscopy (SDPM), which may provide standard Optical Coherence Tomography (OCT) imaging and SDPM imaging simultaneously, enable specific identification of the location and/or orientation of SDPM images, and/or increase the resolution of SDPM images as will be discussed further herein.

Figure 1:
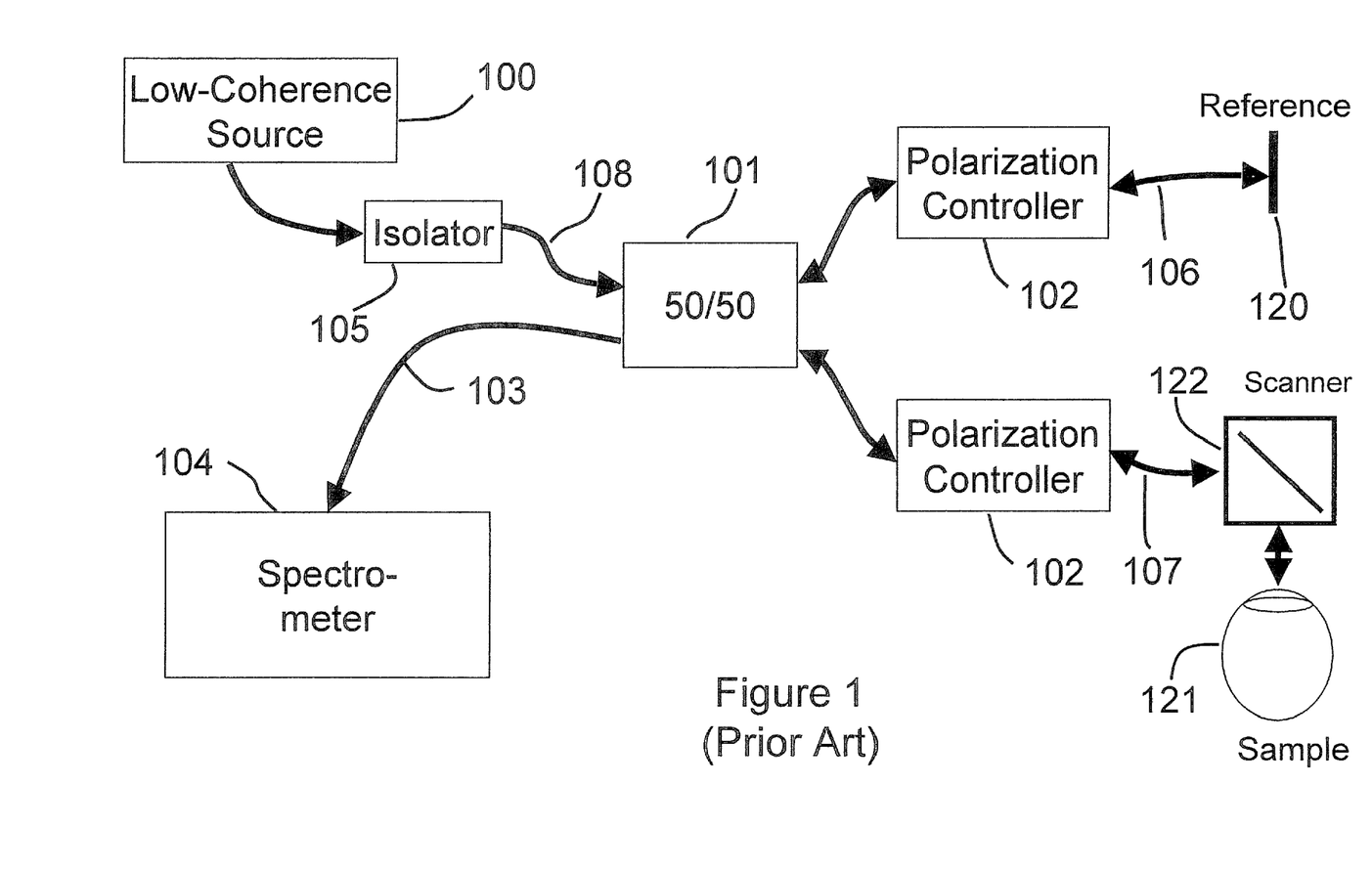
FIG. 1 is a schematic block diagram illustrating conventional Optical Coherence Tomography (OCT) imaging systems.

Referring first to FIG. 1, a general diagram of an optical portion of a Spectral Domain-Optical Coherence Tomography (SD-OCT) system will be discussed. As illustrated in FIG. 1, the SD-OCT system includes a low-coherence source 100, for example, a broadband light source, connected to an interferometer 101, which has a source arm 108, a reference arm 106, a sample arm 107, and a spectrometer arm 103. Connected to the reference arm 106 is a reflective mirror 120, connected to the sample arm 107 is a scanner 122, and connected to the spectrometer arm 103 is spectrometer 104. In some embodiments of the present invention, an optional isolator 105 may be provided in the source arm 108 and one or more polarization controllers 102 may be provided in the source arm 108, reference arm 106, and/or sample arm 107. This system may be capable of acquiring OCT images of the sample 121 with a resolution set by the bandwidth of the broadband source 100 and typically in the range of from about 3.0 to about 20.0 µm.

Figure 2:
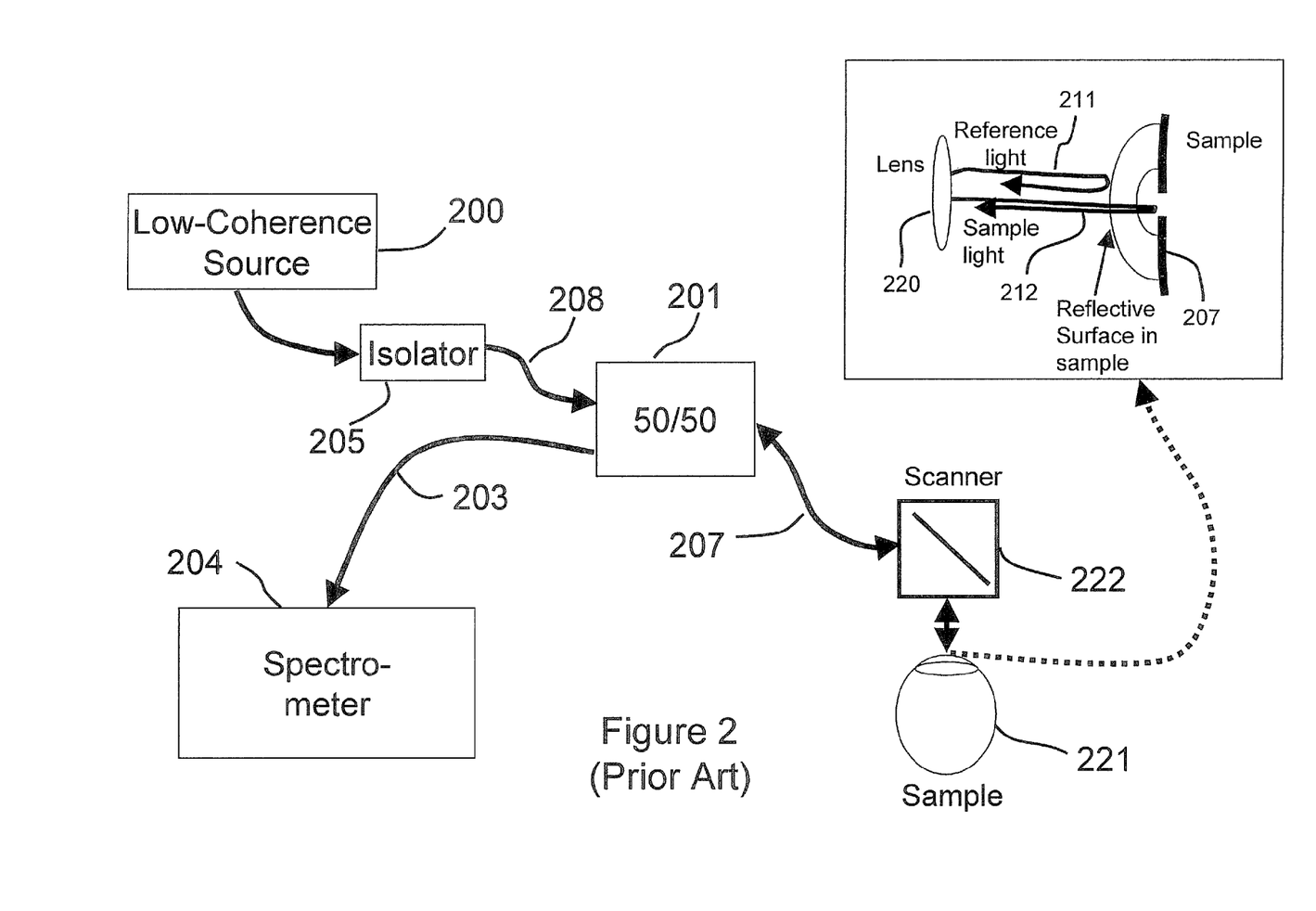
FIG. 2 is a schematic block diagram illustrating a conventional common mode implementation of OCT imaging systems.

Referring now to FIG. 2, like reference numerals refer to like elements throughout, thus, in the interest of brevity, details with respect to like numbered elements of FIG. 1 will not be discussed further herein. As illustrated in FIG. 2, a common mode design may be used for a Spectral Domain-Optical Coherence Tomography (SD-OCT) system. In the common mode implementation, one or more surfaces in the sample 221 may act as the reference reflector instead of having an independent reference arm. The example illustrated in FIG. 2 is a human cornea where the light reflected from the front of the cornea acts as the reference light 211 and light reflected from other depths in the eye are the sample light 212. This technique typically works best where there is a clear interface that provides a reasonably strong reflection. For example, this technique may work well in eyes (human and animal), glass of any form, and plastics.

In some embodiments of the present invention, the reference reflector may be outside of the sample. In these embodiments, the reference reflector is typically very close to sample. For example, a reference reflector outside the sample may be a partially reflective mirror that is just in front of the sample or a coated fiber tip that is scanned over the surface of the sample.

It will be understood that although the example illustrated in FIG. 2 is a human cornea, embodiments of the present invention are not limited to this configuration.

The common mode implementation may have some advantages over implementations with separate sample and reference arms. Since the sample and reference light travel down the same path except for the extra path length that the sample light traverses in the sample, both paths may have very similar attenuation, polarization effects, dispersion effects, and environmental effects, such as thermal, vibrations, and the like.

SDPM takes advantage of this high level of stability between the reference and sample paths to generate image information based on the phase variation of the reference and sample light. By looking at changes in the phase over time or space, subresolution variations can be detected, imaged, and measured. Instead of the from about 3.0 to about 10.0 µm resolution images, SDPM typically can measure changes with a resolution of about 1.0 nm or better. SDPM is not imaging features, but rather is measuring changes in relative path lengths either over time or space. This technique may be well suited to the SD-OCT and SS-OCT systems due to their intrinsic phase stability and the fact that they can be used in common mode system architectures.

It will also be understood that SDPM can be used with Time Domain OCT (TD-OCT) systems. Implementation in TD-OCT may be difficult due to the large amount of phase noise due to the reference arm changing length and the fact that common mode implementations are difficult. SDPM may also be used with any of the Full Field OCT implementations and particularly with the Full Field OCT implementations that rely on a Swept Source architecture without departing from the scope of the present invention. In Full Field OCT, the system typically has a two dimensional camera, which images some portion of the sample. A swept source laser may be used to generate an A-scan at each pixel on the camera. By comparing adjacent pixels, the sane phase variation data can be generated that is created by sweeping the beam over the sample in the SD-OCT and SS-OCT implementations.

Figure 3:
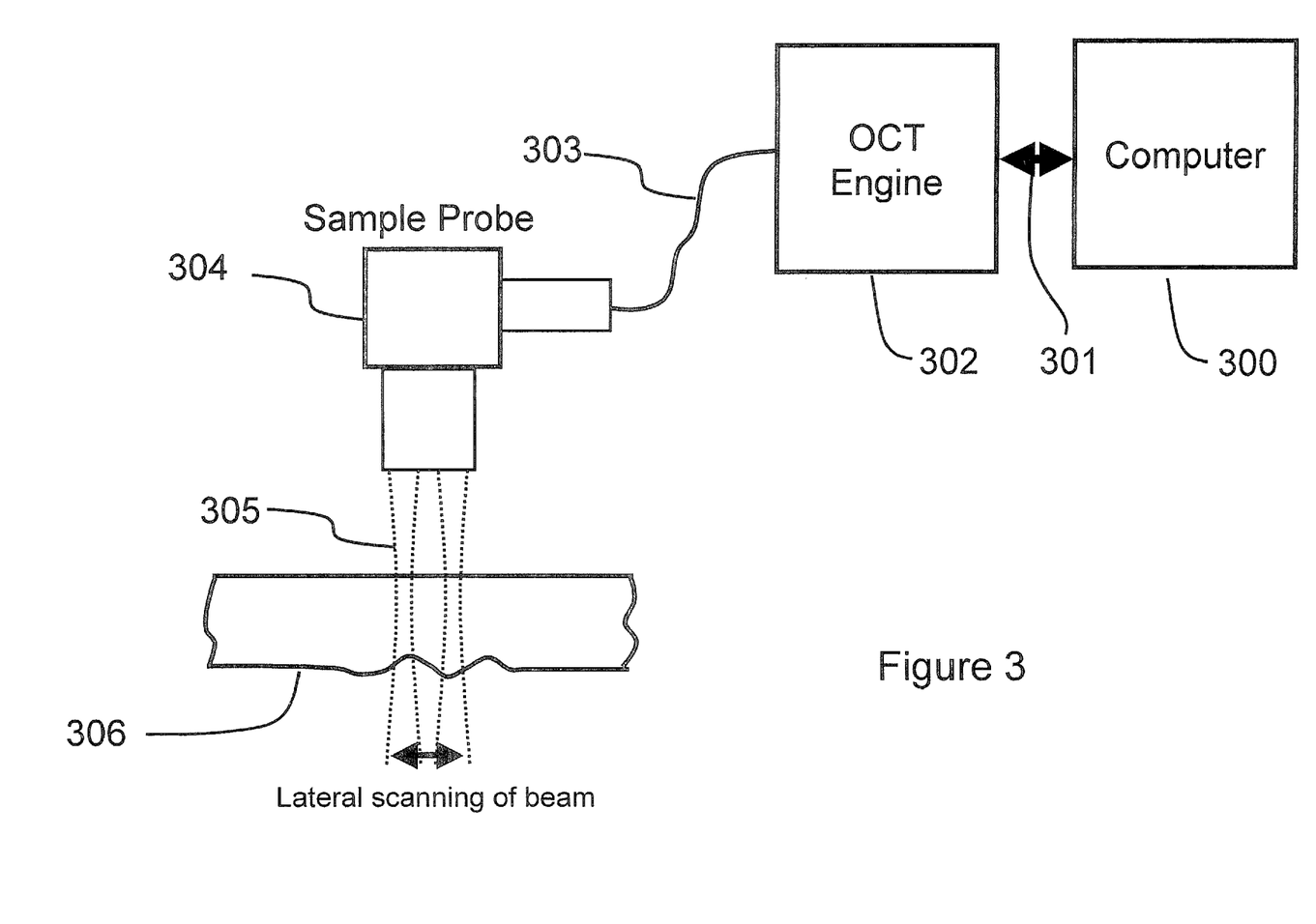
FIG. 3 is a schematic block diagram illustrating a Spectral Domain Phase Microscopy (SDPM) OCT imaging system according to some embodiments of the present invention.

Referring now to FIG. 3, an exemplary implementation of an SDPM system according to some embodiments of the present invention will be discussed. The system illustrated in FIG. 3 includes, an OCT engine 302, for example, the OCT engine of FIG. 2, a computer 300 for control of the system and display of the acquired images and a sample probe 304 for scanning the light beam 305 over the sample 306. In some embodiments of the present invention, the sample may also be scanned underneath a stationary sample probe. The sample illustrated in FIG. 3 is a glass plate 306 with surface imperfections on the bottom surface. By scanning the beam over the sample 306 and measuring phase changes between successive A-scans, the sub-resolution variations in the bottom surface of the glass plate can be imaged and measured. As discussed above, the imaging resolution of the OCT system may be from about 3.0 to about 10.0 µm, but the measurement resolution for variations in the surface may be less than about 1.0 nm.

Figure 4:
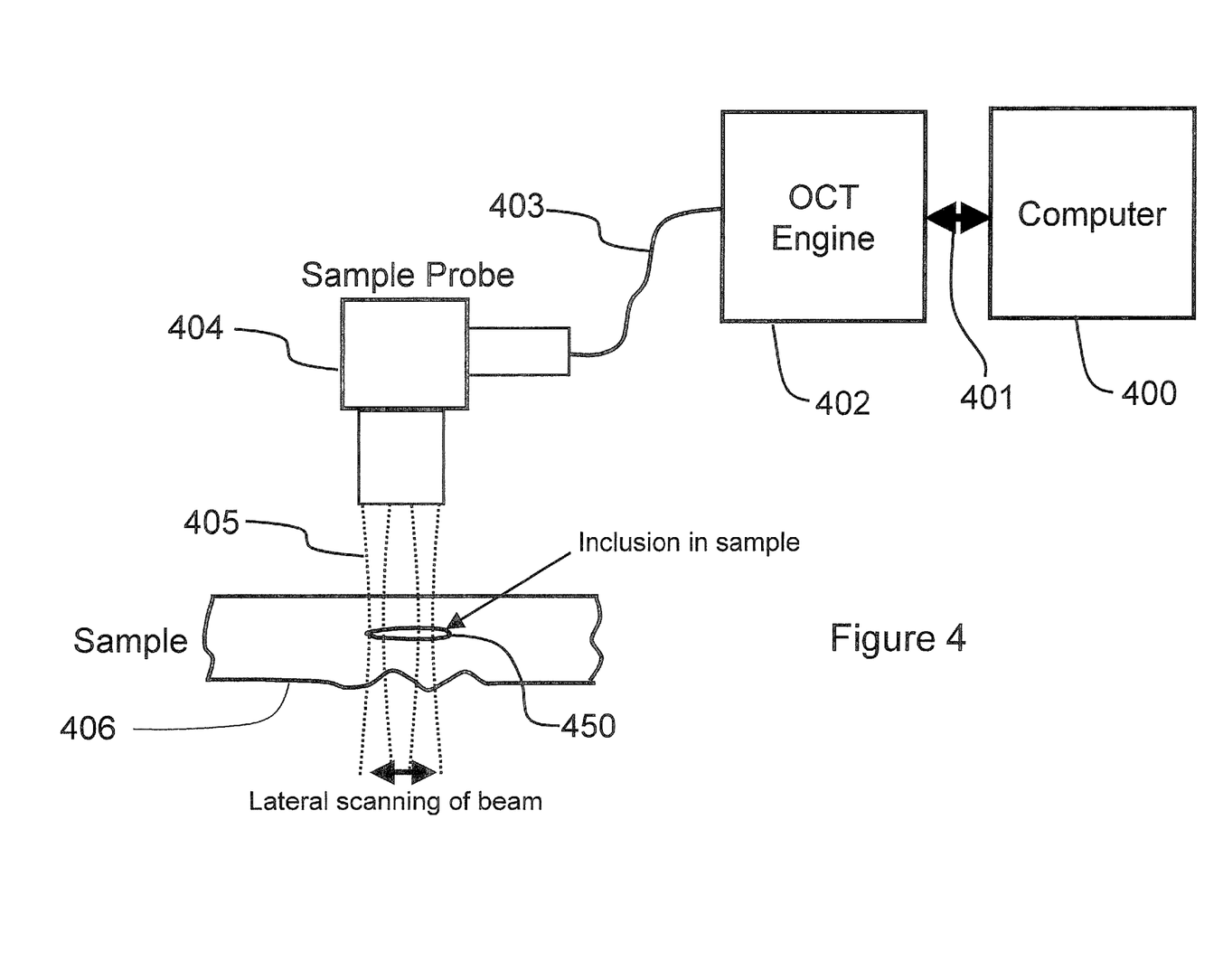
FIG. 4 is a schematic block diagram illustrating an SDPM OCT imaging system according to some embodiments of the present invention.
Figure 5:
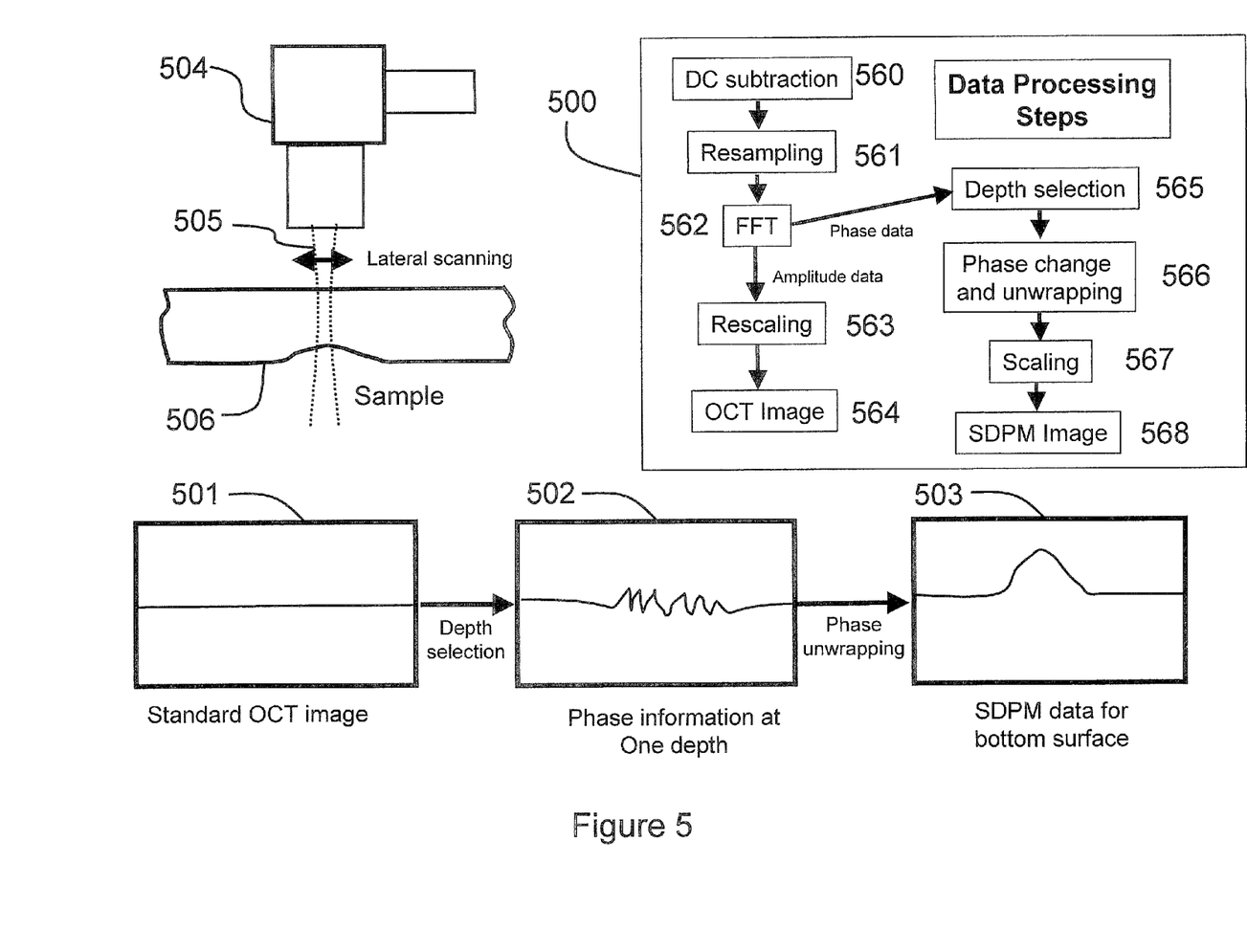
FIG. 5 is a flowchart/diagram illustrating processing steps in the generation of SDPM images according to some embodiments of the present invention.
Figure 6:
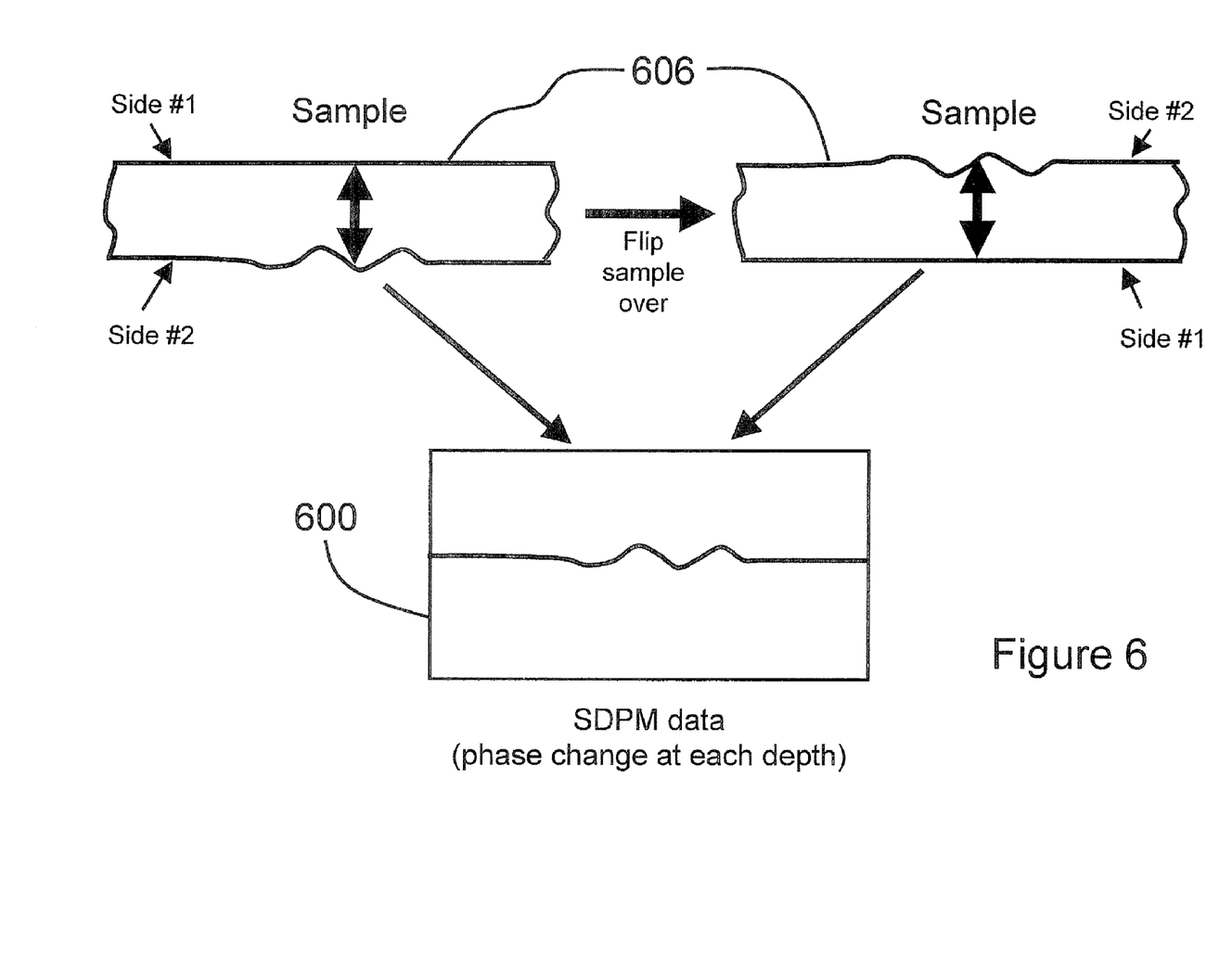
FIG. 6 is a schematic block diagram illustrating image symmetry in SDPM according to some embodiments of the present invention.

Referring flow to FIGS. 4, 5 and 6, OCT/SDPM imaging systems that collect, process and display the data to provide both OCT imaging and SDPM imaging from the same system using the same raw data according to some embodiments of the present invention will be discussed. The system includes a computer 400 or other data processing device coupled to an OCT engine 402 by a communications channel 401. The OCT engine 402 is further coupled to a scanning sample probe 404 by an optical fiber 403. It will be understood that although the connection 403 is discussed herein as being an optical fiber, the connection 403 can be provided by other means than optical means without departing from the scope of the present invention.

The sample probe 404 provides the lateral scanning of the system and may use any scanning system including single mirrors, galvo mirror pairs, MEMS mirrors and/or other beam deflection techniques. The beam 405 scans over the sample and provides image information on both features larger than the OCT resolution, such as the inclusion 450 in the sample 406 and sub-resolution variations within the sample 406, such as the surface variations on the bottom side of the sample 406.

It will be understood that in some embodiments of the present invention, the OCT and SDPM systems may alternatively be configured to provide for lateral scanning of the sample under a stationary sample probe. This arrangement for obtaining lateral information about the sample is equivalent to providing the scanning mechanism in the probe. Thus, as used herein "a scanning sample probe" may include a scanning sample mechanism without departing from the scope of the present invention.

Referring now to FIG. 5, processing steps for the dual OCT/SDPM system according to some embodiments of the present invention will be discussed with respect to the flowchart of block 500. As illustrated in block 500, after raw data is received from the optical portion of the OCT engine, the DC background is subtracted out (block 560), and the data may be resampled (block 561) to convert from sampling in wavelength space to sampling in wavenumber space. Resampling may be used for SD-OCT systems, but may not be needed in all cases including SS-OCT systems with intrinsic sampling in wavenumber. Furthermore, other processing steps may be included to deal with dispersion in the system or other issues without departing from the scope of the present invention.

The data may be Fast Fourier Transformed (FFTed) (block 562) to transform from wavenumber space to physical (or depth) space. The FFT may provide both amplitude data and phase data as illustrated in FIG. 5. In standard OCT systems the amplitude data is further processed via rescaling (block 563) and other processing steps to generate an OCT image (block 564). However, the dual OCT/SDPM systems according to some embodiments of the present invention may further process the phase data to generate a sub-resolution phase change image.

In particular, the phase data may be selected from a particular depth (block 565) in the sample, such as the bottom surface of sample 506, and fed through a phase change and phase unwrapping step (block 566). The result may be appropriately scaled (block 567) and turned into an SDPM image (block 568) that can be displayed to the system user. A graphical representation of the process discussed with respect to block 500 is illustrated by images 501, 502, and 503, where 501 is the standard OCT image for the sample 506, note that the surface variation is not visible in this image since it is sub-resolution, 502 is the raw phase data for the depth of the image corresponding to the bottom surface of the sample 506, and 503 is the unwrapped and scaled data that shows the sub-resolution variation in the bottom surface of the sample 506. Some embodiments of the present invention include the generation of both OCT and SDPM images of the sample 506 for the system user.

Referring now to FIG. 6, consequences of the fact that the SDPM may measure a change in some part of the sample relative to another interface will be discussed. The sample 206 can be imaged with either the flat side (side #1) up or the rough side (side #2) up and in both cases the SDPM image 600 may be the same. The SDPM measures a change or variation in a path length in the sample, in this particular case the variation in the distance from side #1 to side #2, and uses two interfaces or surfaces to generate the path length. SDPM typically cannot inherently distinguish which end of the path length is changing, only that there is some change. Changes in the middle of the path length may also appear in the SDPM image and the location of those changes typically cannot be inherently located.

Figure 7:
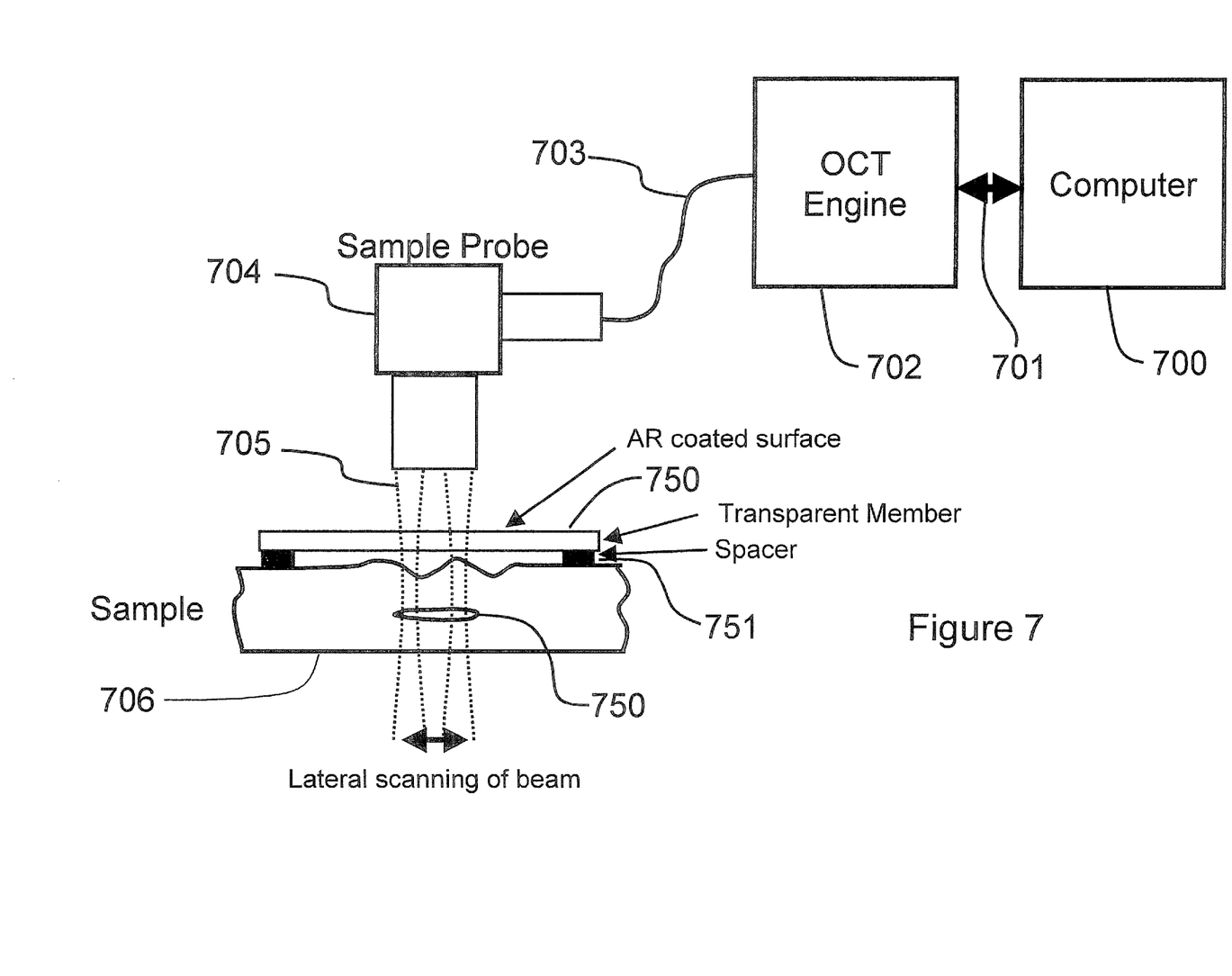
FIG. 7 is a schematic block diagram illustrating SDPM OCT imaging systems including an antireflective slide and spacer according to some embodiments of the present invention.
Figure 8:
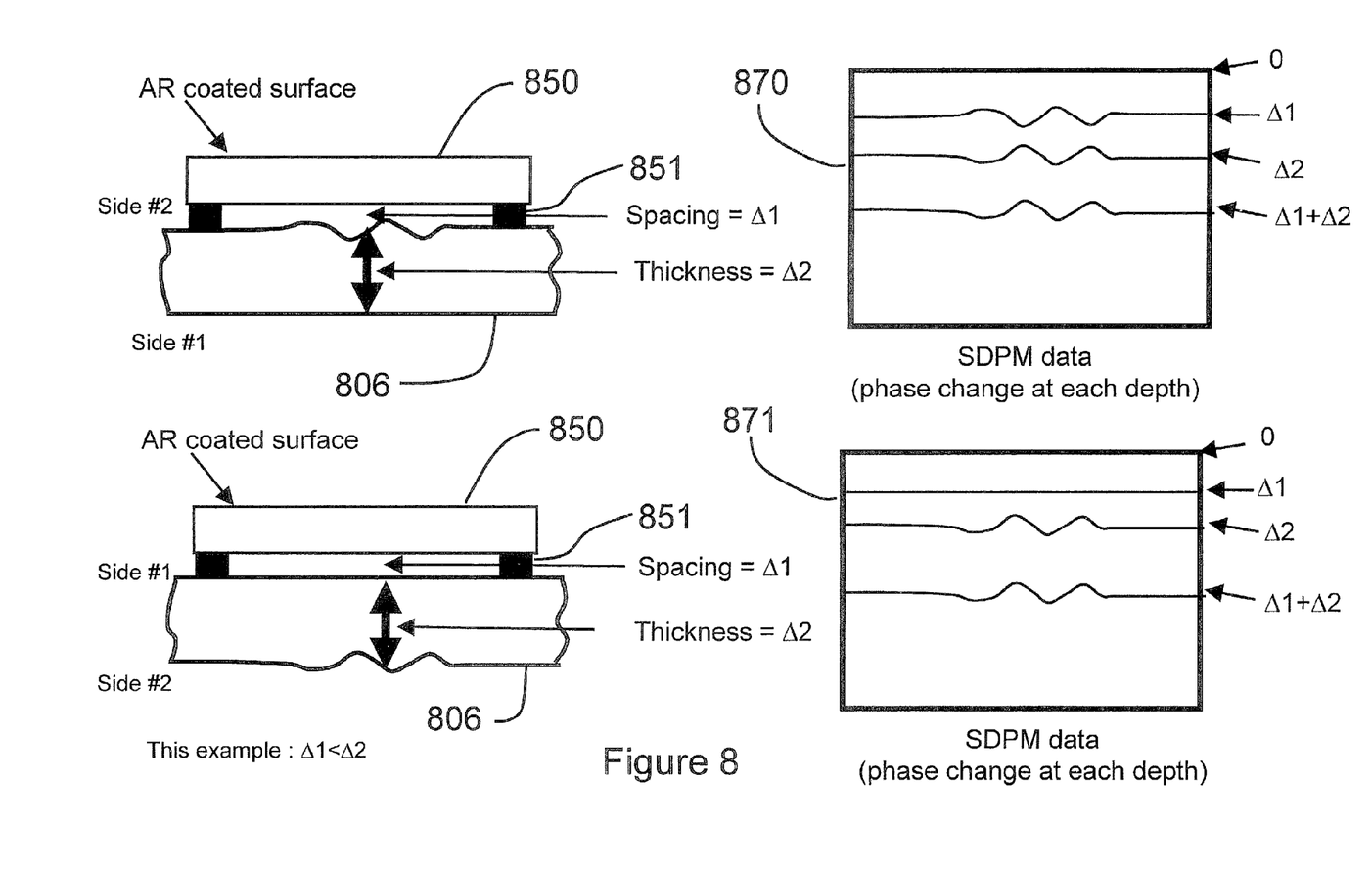
FIG. 8 is a schematic block diagram illustrating SDPM OCT imaging systems according to embodiments of the present invention illustrated in FIG. 7.
Figure 9:
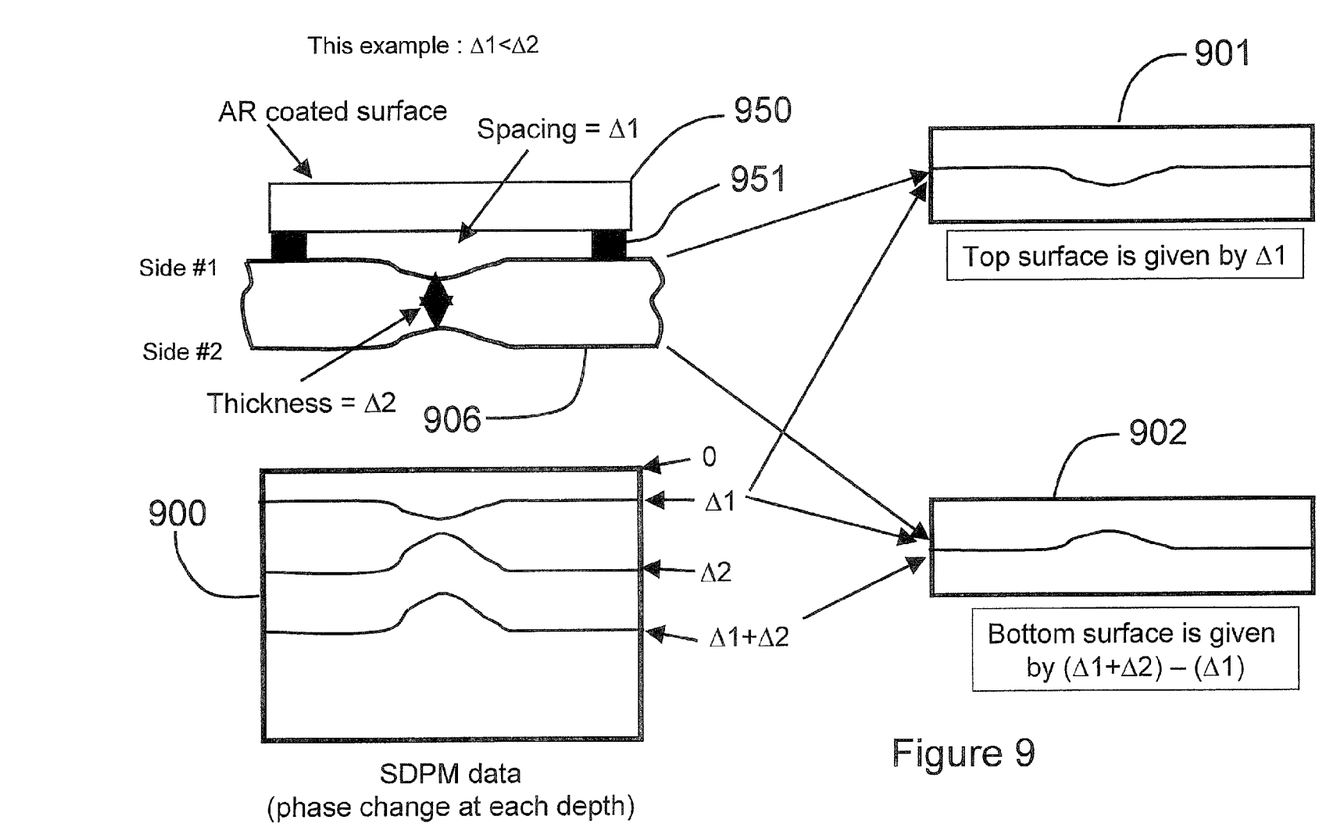
FIG. 9 is a schematic block diagram illustrating SDPM OCT imaging systems according to embodiments of the present invention illustrated in FIG. 7.

Referring now to FIGS. 7, 8, and 9, some embodiments of the present invention that provide a mechanism for addressing the problem of distinguishing which interface in SDPM is changing or if both interfaces are changing at the same time will be discussed. Like reference numerals refer to like elements throughout, thus, details with respect to elements already discussed herein will not be repeated in the interest of brevity. In particular, the system as illustrated in FIG. 7 is similar to the system discussed above with respect to FIGS. 4 through 6, but also includes a transparent member, for example, a glass slide 750 on the sample 706. In some embodiments of the present invention, the glass slide 750 and the sample 706 may be separated by one or more spacers 751. It will be understood that the spacer 751 is optional and is provided for exemplary purposes only. The glass slide 750 may have one or more sides that are anti-reflection (AR) coated and may be positioned on any surface of the sample 706.

Referring now to FIG. 8, the effect of the AR coated glass slide 850 on the SDPM image of the sample 806 will be discussed. The surface of the glass slide 850 that is not AR coated may provide one of the interfaces for the SDPM measurements and various depths in the sample may provide the second interface for each of the SDPM measurements. The top portion of FIG. 8 illustrates the SDPM image 870 generated if the "rough" side (side #2) is up and the bottom portion shows the SDPM image 871 generated if the "rough" side (side #2) is down. In some embodiments of the present invention, the spacing between the glass slide 850 and the sample 806 is less than the thickness of the sample and the surface flatness of the non-AR coated side of the glass slide 850 may be known. It will be understood by those having skill in the art that processing may be simplified if the surface of the glass slide 850 is substantially flat.

As illustrated in the image 870, the top portion where the "rough" side (side #2) of the sample 806 is up generates multiple lines with SDPM data including one at a depth of $\Delta 1$, one at $\Delta 2$, and one at $\Delta 1+\Delta 2$, where $\Delta 1$ is the spacing between the glass slide and the sample and $\Delta 2$ is the thickness of the sample. The SDPM image from depth $\Delta 1$ gives the variation of the bottom surface of the glass slide relative to the top surface of the sample. The SDPM image from depth $\Delta 2$ gives the variation of the top surface of the sample relative to the bottom surface of the sample. The SDPM image from depth $\Delta 1+\Delta 2$ gives the variation of the bottom surface of the glass slide 850 relative to the bottom surface of the sample 806. It will be understood that the variation in the top surface of the sample 806 may show up in the SDPM data at $\Delta 1+\Delta 2$, even though the top surface is not one of the interfaces involved. This may be due to the fact that the SDPM is a measure of the variation in path length between two interfaces and may include all variation in between the two interfaces. Thus, all three depths may return the same SDPM data showing the variation in the top of the sample.

As illustrated in the image 871, in the bottom of FIG. 8 the sample is turned upside down and the smooth surface is now on top. Again multiple SDPM images can be generated. Looking at $\Delta 1$, $\Delta 2$, and one at $\Delta 1+\Delta 2$, there is now a flat line at $\Delta 1$ as the variation in the bottom of the sample, where the "rough" surface (side #2) now is, is only present at $\Delta 2$ and at $\Delta 1+\Delta 2$.

Referring now to FIG. 9, processing steps in accordance with some embodiments of the present invention will be discussed. To complete the picture the sample 906 now has variation in the both the top surface (side #1) and the bottom surface (side #2). Again assume that $\Delta 1$ is less than $\Delta 2$, although that is not a requirement. Graph 900 illustrates the SDPM data, phase change at each depth, graph 901 illustrates the top surface of the sample, and graph 902 illustrates the bottom surface of the sample. SDPM data may be generated at multiple depths, the data from $\Delta 1$, $\Delta 2$, and $\Delta 1+\Delta 2$ is illustrated in graph 900. The variation in the top surface of the sample is just the data at depth $\Delta 1$ as illustrated in graph 901. The SDPM data at $\Delta 2$, and $\Delta 1+\Delta 2$ include variations in both the top and the bottom of the sample as illustrated in image 902. Since the variation in the top surface is now known, it can be subtracted out to leave the variation in the bottom surface. Either data from $\Delta 2$ or $\Delta 1+\Delta 2$ may work, for illustration $\Delta 1+\Delta 2$ is chosen and the data from $\Delta 1$ is subtracted leaving just the variation in the bottom surface of the sample. Thus, it may now be possible to generate SDPM images of the top surface (side #1) and the bottom surface (side #2) of the sample 906 without knowing in advance which side is which, i.e., the sample can be flipped over and accurate images of the top and bottom surface can still be generated.

According to some embodiments of the present invention illustrated in FIGS. 7 through 9, a known interface may be provided that is external to the sample and breaks the intrinsic symmetry in the sample. Once the variation in one surface in the sample is known, it is possible to calculate the variation in other samples by subtracting out known variations to provide data on a new interface. It will be understood that although techniques discussed herein are illustrated with respect to two surfaces in the sample, embodiments of the present invention are not limited to this configuration. For example, three or more interfaces may be provided in the sample without departing from the scope of the present invention. As illustrated, there is little to no variation in the middle of the sample, however, this technique may work for variations in the middle of the sample provided that there is sufficient signal to generate SDPM data at that particular depth in the sample.

Figure 10:
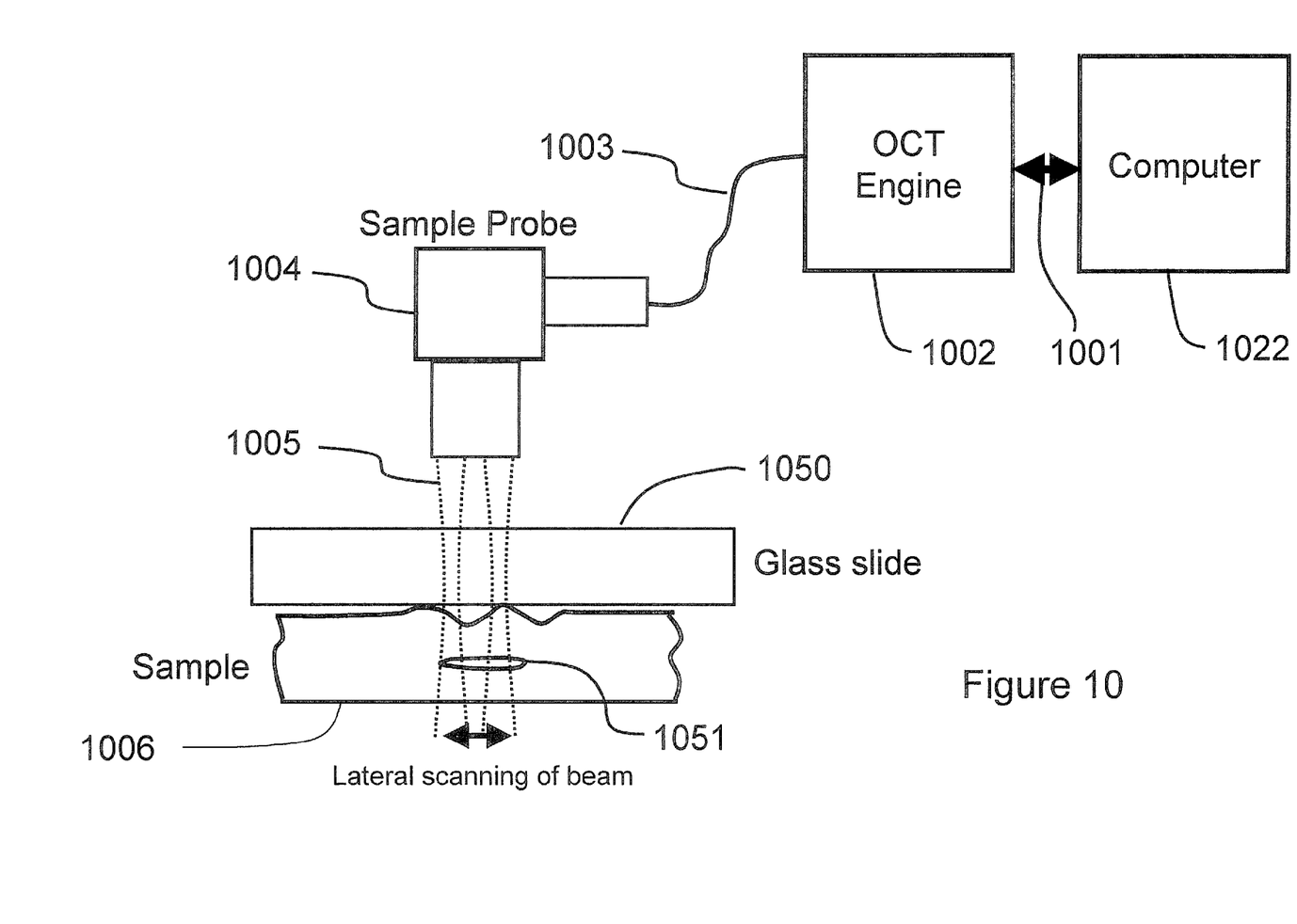
FIG. 10 is a schematic block diagram illustrating SDPM OCT imaging systems according to some embodiments of the present invention.
Figure 11:
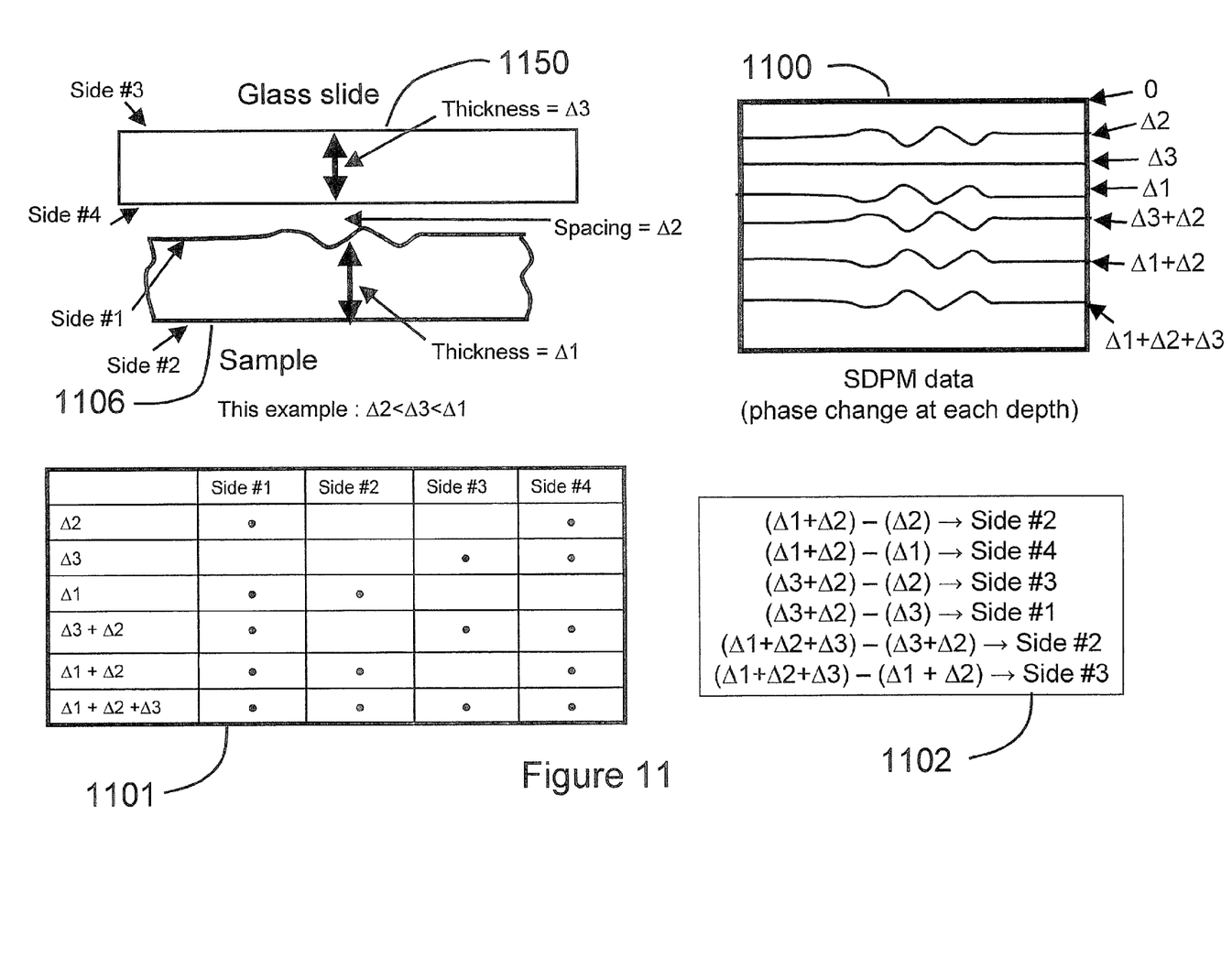
FIG. 11 is a schematic block diagram illustrating SDPM OCT imaging systems according to embodiments of the present invention illustrated in FIG. 10.

Referring now to FIGS. 10 and 11, some embodiments of the present invention having multiple external interfaces will be discussed. Like reference numerals refer to like elements throughout, thus, elements discussed above may not be discussed further herein in the interest of brevity. As an illustrative example, consider FIGS. 10 and 11, where a glass slide 1050/1150 having no AR coating is used. Again the glass slide 1050/1150 can be placed on any surface of the sample, as illustrated it is shown above the sample 1006/1106. It will be understood that although embodiments of the present invention illustrated in FIGS. 10 and 11 do not include a spacer between the sample 1006/1106 and the glass slide 1050/1150, embodiments of the present invention are not limited to this configuration. A spacer can be used as discussed above without departing from the scope of the present invention.

As illustrated in FIG. 11, both sides (sides #3 and #4) of the glass slide 1150 can act as interfaces, thus, there are more depths in the OCT image that may provide SDPM data and images. Assume for illustration that the thickness of the sample 1106 is $\Delta 1$, the gap between the sample and the glass slide is $\Delta 2$, the thickness of the glass slide is $\Delta 3$ and that $\Delta 2 < \Delta 3 < \Delta 1$. This technique may work for SDPM data generated at numerous depths including $\Delta 2$, $\Delta 3$, $\Delta 1$, $(\Delta 3+\Delta 2)$, $(\Delta 1+\Delta 2)$, and $(\Delta 1+\Delta 2+\Delta 3)$ as shown in the graph 1100. This SDPM data may be generated by four sides numbered #1, #2, #3, and #4, assuming no variations in between the sides. Table 1101 shows which SDPM data sets contain information about each surface. For example, the SDPM data from depth $\Delta 1+\Delta 2$ may have information about side #1, side #2, and side #4. Box 1102 shows the calculations that may be used according to some embodiments of the present invention to extract information about a particular side from the SDPM data generated. For example, the variation in side #1 can be calculated by taking the SDPM data from depth $(\Delta 3+\Delta 2)$ and subtracting depth $\Delta 3$.

There are multiple ways to calculate the SDPM data for some surfaces, for example, SDPM data for side #2 can be calculated from either $(\Delta 1+\Delta 2)-(\Delta 2)$ or $(\Delta 1+\Delta 2+\Delta 3)-(\Delta 3+\Delta 2)$. Note that this technique may work even if $\Delta 2$ is very small, as in the case where the glass slide is touching the sample. Provided the variation in side #4 is known, the variation in side #1 and side #2 can still be determined from SDPM data from $\Delta 3$, which now contains information about side #1, and data from $(\Delta 1+\Delta 2+\Delta 3)-(\Delta 3)$, which provides the information about side #2.

Figure 12:
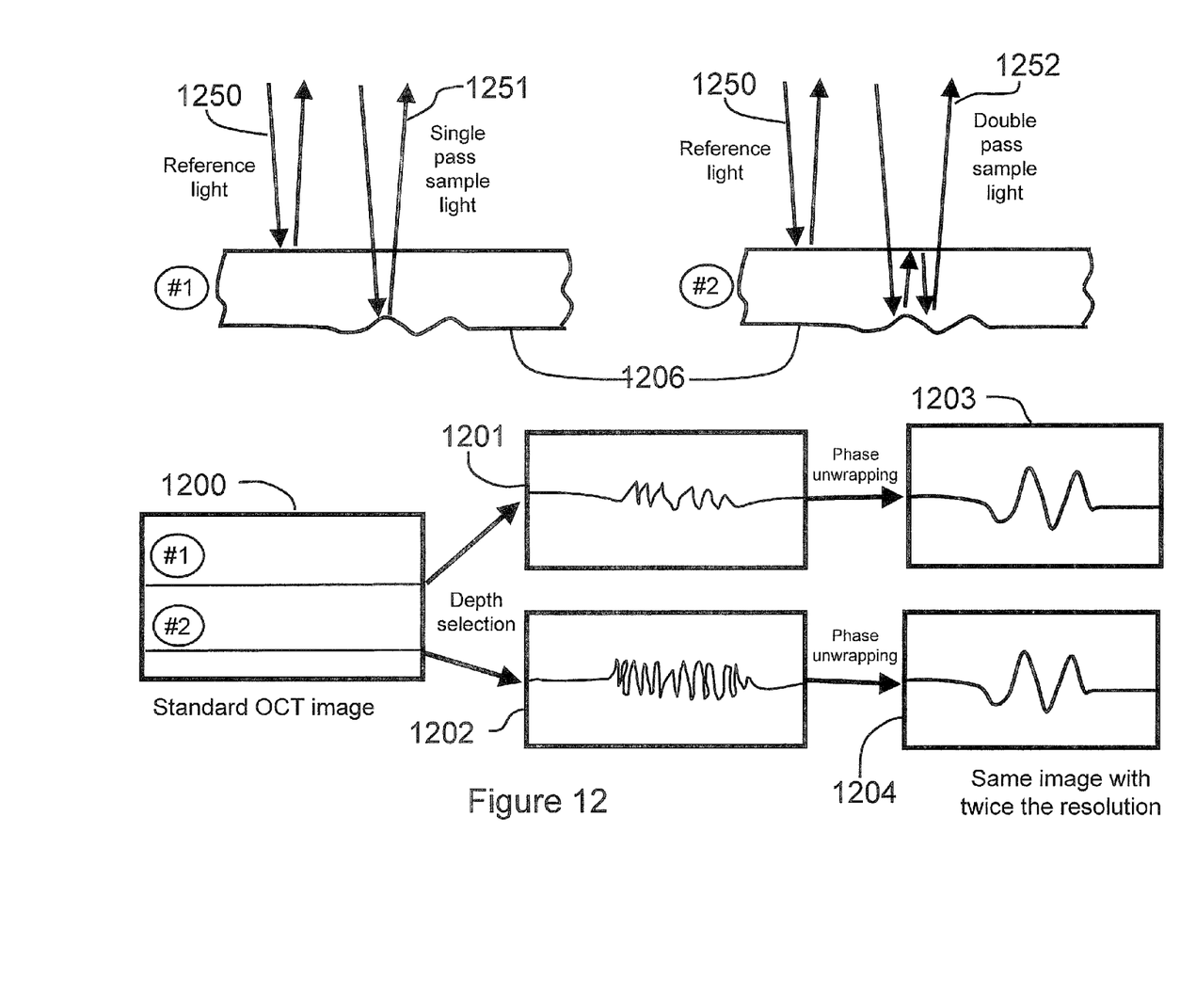
FIG. 12 is a schematic block diagram illustrating SDPM OCT imaging systems according to some embodiments of the present invention.

Referring now to FIG. 12, a technique for acquiring higher resolution SDPM images from a sample 1206 will be discussed. Embodiments of the present invention discussed above have primarily been for the case where the sample light makes a single roundtrip 1251 through the sample as is illustrated in the upper left in diagram #1. OCT images may also be generated by light that makes multiple roundtrips through the sample as illustrated by the light path 1252 illustrated in diagram #2. The standard OCT image 1200 contains image data from the single pass case, the double pass case, and possibly others. Typically the SDPM image is generated from the single pass case as is shown in 1201 and 1203. However, the technique may work for sample light that takes any number of roundtrips, as illustrated in the double pass case in 1202 and 1204. Since this light is reflected off of the "rough" surface twice instead of once, it may experience twice as much path length variation and, thus, may generate SDPM images with twice the resolution. This may be countered by generally higher noise at deeper levels in the OCT and the inherent imaging depth limit of the OCT system.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An optical coherence tomography (OCT) system comprising:
   an OCT engine configured to provide both standard OCT imaging and spectral domain phase microscopy (SDPM) imaging, obtain image data associated with a first pass through a sample and obtain image data associated with a second pass through the sample;
   a processor coupled to the OCT engine and configured to process the image data associated with the first and second passes through the sample to determine a path length variation and provide an image having a resolution based on the determined path length variation;
   a transparent member positioned on the sample;
   a sample probe and a sample stage configured to provide lateral scanning of the sample through the transparent member and provide image information associated with the sample such that image information associated with a first surface of the sample can be distinguished from image information associated with a second surface of the sample; and
   at least one spacer positioned between the transparent member and the scanning sample, wherein a distance provided by the at least one spacer between the sample and the transparent member is used to distinguish between the image information associated with a first surface of the sample and the image information associated with a second surface of the sample.

2. The system of claim 1, wherein the processor is further configured to use a first signal processing method when the OCT engine is configured to provide standard OCT imaging and a second signal processing method when the OCT engine is configured to provide SDPM imaging.

3. The system of claim 1, wherein the distance between the sample and the transparent member is less than a thickness of the sample.

4. The system of claim 1, wherein the transparent member has a thickness that is greater than a thickness of the sample.

* * * * *